United States Patent [19]

Arcas et al.

[11] Patent Number: 4,768,379

[45] Date of Patent: Sep. 6, 1988

[54] METHOD AND APPARATUS FOR DETERMINING FLOW RESISTANCE OF FULLY ASSEMBLED ACOUSTIC LINERS

[75] Inventors: Noe Arcas, Plainview; Joseph P. Gow, Huntington; Charles A. Parente, Oyster Bay, all of N.Y.

[73] Assignee: Grumman Aerospace Corporation, Bethpage, N.Y.

[21] Appl. No.: 890,999

[22] Filed: Jul. 25, 1986

[51] Int. Cl.[4] ............................................. G01N 29/04
[52] U.S. Cl. ........................................ 73/589; 73/588
[58] Field of Search ................... 73/599, 583, 589, 579

[56] References Cited

U.S. PATENT DOCUMENTS

| | | | |
|---|---|---|---|
| 2,981,096 | 4/1961 | Carrell | 73/589 |
| 3,288,241 | 11/1966 | Bancroft et al. | 73/589 |
| 3,658,147 | 4/1972 | Ho et al. | 73/659 |
| 3,824,842 | 7/1974 | Wirt et al. | 73/589 |
| 3,883,841 | 5/1975 | Norel et al. | 73/589 |
| 3,960,004 | 6/1976 | Wirt et al. | 73/589 |
| 4,249,422 | 2/1981 | Gaunaurd et al. | 73/589 |
| 4,283,953 | 8/1981 | Plona | 73/589 |
| 4,305,295 | 12/1981 | Andersson et al. | 73/589 |
| 4,397,187 | 8/1983 | Stribling | 73/589 |
| 4,403,508 | 9/1983 | Langlois | 73/589 |
| 4,463,453 | 7/1984 | Cohen et al. | 73/583 |
| 4,537,630 | 8/1985 | Syed | 73/589 |

FOREIGN PATENT DOCUMENTS 714660  8/1980  U.S.S.R. ..

OTHER PUBLICATIONS

Dean, "An In Situ Method of Wall Acoustic Impedance Measurement in Flow Ducts", J. of Sound & Vibration, vol. 34, No. 1, pp. 97–130, May 1974.
Blaser, D. A. and Chung, J. Y., "Transfer Function Method of Measuring In-Duct Acoustic Properties. I. Theory", J. Acoust. Soc. Am., vol. 68, No. 3, Sep. 80, pp. 907–913.
Syed, Asif A., "Acoustic Impedance Measurement System (AIMS)", Noise-Con, Jun. 1985, pp. 93–98.
Seybert, A. F. and Soenarko, Benjamin, "Error Analysis of Spectral Estimates with Application to the Measurement of Acoustic Parameters using Random Sound Fields in Ducts", J. Acoust. Soc. Am., vol. 69, No. 4, Apr. 1981, pp. 1190–1199.
Ross, D. F. and Seybert, A. F., "Experimental Determination of Acoustic Properties Using a Two-Microphone Random-Excitation Technique", J. Acoust. Soc. Am., vol. 61, No. 5, May 1977, pp. 1362–1370.
Blaser, D. A. and Chung, J. Y., "Transfer Function Method of Measuring In-Duct Acoustic Properties. II. Experiment", J. Acoust. Am., vol. 68, No. 3, Sep. 80, pp. 914–921.

Primary Examiner—Stewart J. Levy
Assistant Examiner—Louis M. Arana
Attorney, Agent, or Firm—Richard G. Geib; Daniel J. Tick; David Aker

[57] ABSTRACT

Apparatus and method for determining the steady state flow resistance of face sheets on fully assembled acoustic duct liners. Resistance is measured by subjecting the liner to a sinusoidal acoustic pressure field at the face sheet surface. The pressure field is applied through a cylindrical waveguide and is measured by a pressure transducer flush mounted on the inside of the waveguide near the liner face. A second pressure measurement, obtained by a similar transducer positioned further from the face, is combined with the first measurement to calculate the acoustic resistance for the excitation frequency. If the excitation frequency coincides with the resonant frequency of the liner configuration, then no significant pressure exists on the back surface of the liner face sheet. For this condition the root mean square (rms) pressure measured at the face sheet is equated to the static pressure drop used to obtain the steady state flow resistance. The rms velocity of the oscillating pressure wave is calculated from the ratio of the rms pressure to resistance. A repetition of the procedure for several magnitudes of dynamic pressure permits the development of a curve which describes the non-linear characteristics of resistance with changes in velocity. This curve may be equated to a similar curve obtained using steady state flow resistance measurements of the liner in its partially assembled state without a backing surface.

25 Claims, 7 Drawing Sheets

——————— DC FLOW TEST AREA
— — — — TWO MICROPHONE TEST AREA

RESISTANCE CALIBRATION PROCEDURE

METHOD AND APPARATUS FOR DETERMINING FLOW RESISTANCE OF FULLY ASSEMBLED ACOUSTIC LINERS

BACKGROUND OF THE INVENTION

The present invention relates to a method and apparatus for determining the flow resistance of acoustically absorbing material. More particularly, it relates to a method and apparatus for determining the flow resistance of fully assembled acoustically absorbing duct liners by using a sinusoidal acoustic pressure in the absence of grazing air flow parallel to the liner surface.

Single degree of freedom sound absorptive duct liners currently used on aircraft engines consist of a face sheet bonded to cellular material such as honeycomb which is itself bonded to a solid back sheet. The face sheet may consist of a perforated skin or a woven wire cloth material bonded to a perforated skin. The latter construction is currently termed a "linear liner" throughout the aircraft industry. The flow resistance of linear liners has shown a high degree of insensitivity to the presence of air flow along the face sheet surface of the liner. Such flow is present within engine ducts during aircraft operation.

The acoustic properties of a liner are greatly influenced by the face sheet resistance. The resistance of the face sheet of a linear liner is measured using conventional methods and apparatus by performing a DC (i.e. Direct Current or steady state) flow resistance measurement. The woven wire mesh side of the face sheet is subjected to a steady air flow normal to its surface. In many instances, the effect of perforate hole blockage due to the bond between the face sheet and cellular honeycomb is incorporated by performing the measurement on the face sheet/honeycomb construction without the presence of the back sheet. The ratio of pressure drop across the face sheet to steady air flow velocity measured upstream of the face sheet determines its DC flow resistance.

A similar type of measurement can be performed on a non-linear type construction, perforated face sheet without the woven wire cloth. However, the resistance of non-linear liners has been determined to be highly influenced by the presence of grazing air flow. The resistance measured for such a construction would be indicative of its behavior only in the absence of grazing flow.

The DC flow resistance for a given flow velocity and its variation with velocity (defined as the non-linearity) is used to insure compliance with quality assurance criteria.

The DC flow resistance measurement can only be made on the face sheet itself without the presence of the back sheet structure because the back sheet would interfere with the flow of air. The requirement of a DC flow resistance measurement on partially assembled liners impedes the manufacturing process and imposes restrictions on the number of bond cycles required for construction. Such restrictions make it highly advantageous to develop a procedure for evaluating flow resistance of fully assembled liners.

The principal object of the present invention is to provide a method and an apparatus for determining the flow resistance of a fully assembled liner including a face sheet, honeycomb core and back sheet.

An object of the invention is to provide a method and apparatus for determining the non-linearity of a fully assembled liner.

Another object of the invention is to provide a method and apparatus wherein data obtained concerning the acoustic absorbing properties of a liner can be used to determine the mass reactance of the face sheet of the liner.

Still another object of the invention is to provide an automated method and apparatus for determining flow resistance capable of being operated by assembly line production personnel.

A further object of the invention is to provide a method and apparatus for determining flow resistance and non-linearity at a liner production facility for the purpose of monitoring quality assurance criteria.

Yet another object of the invention is to provide a method and apparatus which supplies a detailed permanent record of all measurements performed on an assembled liner.

A further object of the invention is to provide a method and apparatus for determining flow resistance and non-linearity of an assembled liner installed on an aircraft so as to determine the degradation in resistance and non-linearity of the liner resulting from in-service usage.

A further object of the invention is to provide a method for compensating for measurement error introduced by such factors as honeycomb cell misalignment with the waveguide used for measurement, transverse propagation of acoustic energy through cell walls, the presence of water drainage holes extending into adjacent cells outside the boundaries of the waveguide and transmission of acoustic energy through the liner back sheet, when using acoustic oscillatory pressures instead of static pressures.

SUMMARY OF THE INVENTION

In accordance with the invention, which contemplates a method and an apparatus, the acoustic resistance of a sound absorbing material at a velocity is determined by placing an open end of an acoustic waveguide in contact with the sound absorbing material. The waveguide is excited with an acoustic signal by an acoustic signal generating means. Pressure transducers, such as microphones, are used to determine the acoustic pressure level at a first point and at a second point along the waveguide proximate the open end thereof. A calculating means calculates an acoustic impedance based on values of the pressures measured at the first point and the second point to define the resistance. The calculating means divides the pressure at the first point by the acoustic impedance to determine the equivalent corresponding velocity.

An amplitude adjusting means is used to adjust the amplitude of the acoustic signal to thereby vary the equivalent velocity. The acoustic resistance is measured for at least two different velocities so as to define a non-linearity factor. A frequency adjusting means permits the frequency of the acoustic signal to be adjusted to the resonant frequency of the liner.

The apparatus and method are used to measure the acoustic resistance of a fully assembled liner which includes a face sheet, a honeycomb layer and a back sheet.

Absolute sound pressure level calibration factors for the method and apparatus are established by exposing both microphones to a known sound pressure level as, for example, by placing both microphones and a fully calibrated reference microphone in the same acoustic pressure field. The absolute magnitude and phase differences between the two transducers are determined by mounting the transducers in a coherent acoustic field, such as, for example, side by side in openings in an acoustically reflective material which is acoustically sealed to the open end of the waveguide. The acoustic driver is activated at the test frequency and pressure levels, and data indicative of the response characteristics are stored.

A test calibration sample of known and unchanging acoustic characteristics is then coupled to the open end of the waveguide. The acoustic properties of this sample are measured with the system. The complex frequency response measurement data is then divided by the stored transducer magnitude and phase data to define a corrected frequency response function for the sample at the frequency and sound pressure levels of interest. The response function is stored within the system.

The corrected frequency response function is later used for field calibration. The sample is placed over the open end of the waveguide. The apparent frequency response function is measured at each pressure level. This data is divided by the actual frequency response determined with the test sample under laboratory conditions. The result is a complex number which describes the magnitude and phase difference between the transducers so as to correct for changes in ambient conditions such as temperature or humidity.

As a final correction procedure, the DC flow resistance and non-linearity of a liner sample identical in construction to the fully assembled liner is measured without a backing sheet in place. The backing sheet is then installed using assembly procedures and materials identical to those used for full scale production liners. The open end of the acoustic waveguide is positioned against the sample face sheet and response function measurements are made. The response function is adjusted to account for magnitude and phase differences between the transducers by using results obtained from the previous calibration procedures. The corrected frequency response function is then used to determine the acoustic resistance at each acoustic pressure level. A straight line curve fit through these data points is numerically corrected to match the DC flow data.

BRIEF DESCRIPTION OF THE DRAWINGS

In order that the invention may be readily carried into effect, it will now be described with reference to the accompanying drawings, wherein.

DETAILED DESCRIPTION OF THE PREFERRED EMBODIMENT

Figure 1:
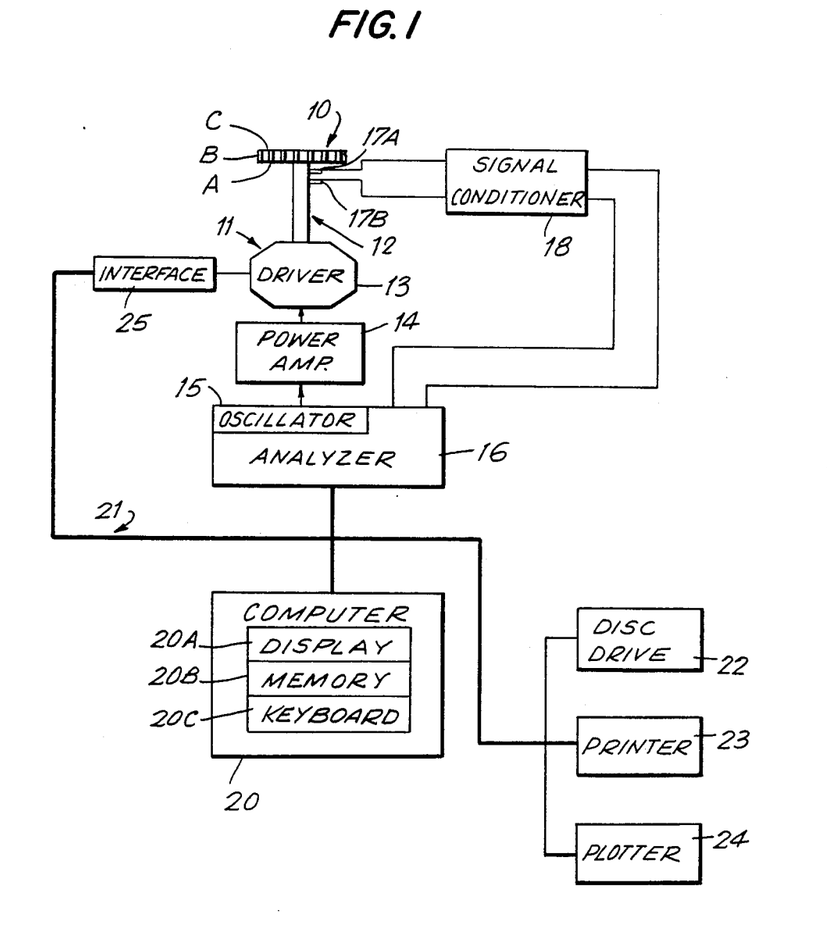
FIG. 1 is a block diagram of the apparatus according to the invention.

FIG. 1 is a block diagram showing the various components of the apparatus according to the invention as used to determine the resistance of a liner. The liner 10 undergoing measurement consists of a face sheet A, a honeycomb interior B, and a back sheet C. Liner 10 is positioned against a test head 11 which includes a waveguide 12 coupled to an acoustic signal generator 13. Power to the signal generator 13 is supplied by an amplifier 14 which amplifies the electrical oscillator output of a programmable oscillator 15 within a dual channel spectrum analyzer 16 thus providing an acoustic pressure field within waveguide 12.

Two microphones 17A and 17B are mounted along tube 12, as more fully described below. The signal outputs of microphones 17A and 17B are connected to a dual channel signal conditioner 18. Signal conditioner 18 provides a polarizing voltage to each of microphones 17A and 17B and pre-amplifies the output signals thereof. The outputs of signal conditioner 18 are connected to signal inputs of dual channel spectrum analyzer 16 which may be a Hewlett Packard Model 3562A.

A controller or microcomputer 20 is interfaced through a series of IEEE type 488 interface cables or buses 21 to dual channel spectrum analyzer 16, disc drive 22, printer 23 and plotter 24. Disc drive 22, printer 23 and plotter 24 are used for data storage, printout of test results and graphic representation of test data, respectively. Microcomputer 20 may be a Hewlett Packard 200 Series 9816 which includes a display 20A and an internal memory 20B and is interfaced to a keyboard 20C.

The system of FIG. 1 may be designed for automated production testing. Computer 20 controls system operation, performs mathematical operations, and prompts the operator by means of display 20A for data entry and provides procedural instruction. Keyboard 20B, mounted in a slide mount, facilitates entry of necessary information. Printer 23, also mounted on a slide mount, outputs test results in tabular formats, while plotter 24 is used for graphic formats. Use of a printer with appropriate capability permits combining the functions of printer 23 and plotter 24. A control system interface 25 transfers control of the measurement procedure to a control panel located on the test head 11 as more fully described with reference to FIG. 2B.

Figure 2A:
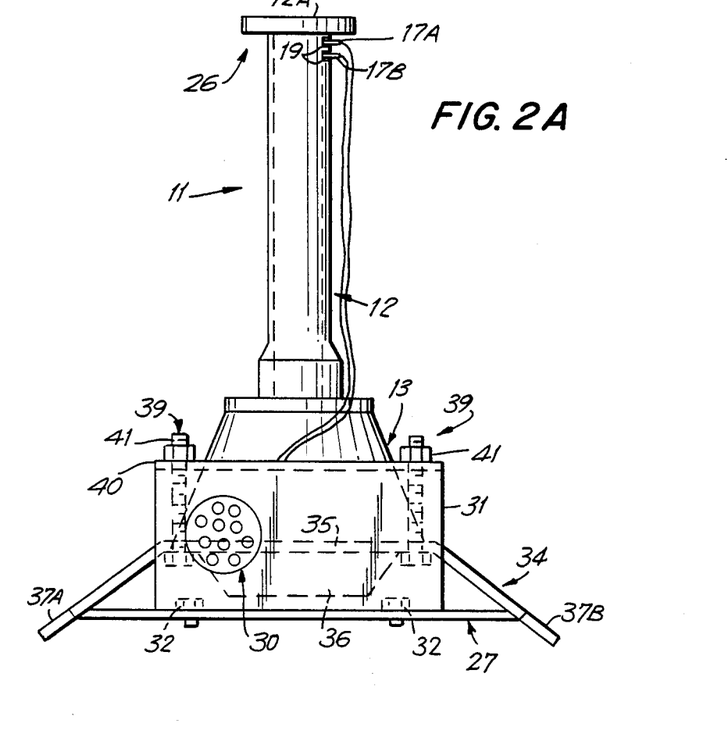
FIG. 2A is a side elevational view of the test head used in the system of FIG. 1.

Referring to FIG. 2A, the test head 11 includes cylindrical waveguide 12 which is a tube with an inside diameter of 1.2 inches and a length of 6 inches. These dimensions are selected to allow for the highest possible sound pressure level at the open end 12A of waveguide 12 while assuring that the wave propagation is planar in the frequency range of interest, which is between 800 and 6000 Hz. A flexible hard rubber gasket 26 seals the end of waveguide 12 against liner 10 even when the surface of liner 10 is moderately curved so as to have a radius of curvature of approximately twenty one inches or greater. Gasket 26 has an outside diameter which is larger than the diameter of waveguide 12. This seals the perforated openings to the cells surrounding the test area covered by the inside diameter of waveguide 12 and serves to minimize any losses of acoustic energy associated with transverse propagation through the cell walls.

The two pressure transducers or microphones 17A and 17B are mounted in openings in the wall of waveguide 12 flush with the interior wall thereof. Microphones 17A and 17B are secured in their respective openings by a thin annular layer 19 of RTV rubber which is flexible enough to provide a seal to waveguide 12 so as to prevent the leakage of acoustic energy, thus preventing the presentation of uncorrelated signals to microphones 17A and 17B. Further, each layer 19 prevents transverse propagation of sound or vibration by acting as an isolator so that noise signals and vibration traveling along the wall of waveguide 12 are not significantly represented in the output of microphone 17A and 17B. Finally, the use of layer 19, rather than a more rigid or stronger material, facilitates replacement of a microphone if it becomes defective.

Microphones 17A and 17B are selected so that the diameter of the face of the microphones is minimized to reduce the possibility of measurement error caused by a pressure gradient across the face. A microphone meeting these requirements is the Kulite Model XCS-093. This is a transducer with a range of up to 2 psig and a nominal sensitivity of 300 mV/PA. Microphone 17A is located near the open end 12A of waveguide 12 and thus near the liner face sheet A (FIG. 1). Microphone 17A is positioned at a distance of 0.21 inch from the liner face sheet as measured from the liner face sheet to the microphone center. This location provides an accurate reading of the sound pressure at the face sheet while assuring that the measurement is free of localized pressure disturbances caused by oscillating air masses in the immediate area of the liner face due to near field effects of holes in the face sheet. Extensive laboratory testing has demonstrated that localized pressure disturbances are no longer present at a distance of four times the dimension of openings in the face sheet. Due to the inertia of the air mass within the face sheet, the maximum in the standing wave pattern is actually shifted back away from the face sheet, so that taking measurements at this point is advantageous.

Microphone 17B, located farthest from the sample face, is positioned at a location which is determined from knowledge of the resonant frequency of the liner to be tested. It should be mounted no less than 0.4 inch and no more than 1.2 inch from the center of microphone 17A. Microphone 17B should not be located at any position such that the ratio of one quarter of the test frequency wavelength to transducer center to center spacing is an integer. This criteria assures good coherence between the two pressure measurements.

Acoustic pressure driver 13 is fastened to waveguide 12 by a threaded joint (not shown) at the mouth of driver 13. Sound waves propagate from driver 13 through an exponential expansion into waveguide 12. Acoustic driver 13 should be capable of generating high intensity acoustic pressures at the excitation frequency. It is also desirable that the frequency response of acoustic driver 13 be fairly constant over an 800 to 6000 Hz frequency range. One such driver is the Photocon PS-140. It is a 100 Watt, 16 Ohm high intensity driver with exceptional response characteristics.

Figure 2B:
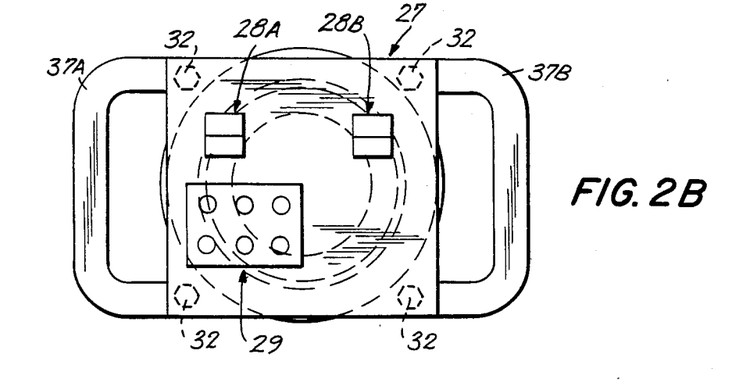
FIG. 2B is a bottom, plan view of the test head illustrated in FIG. 2A.

Referring to FIG. 2B, a control panel 27, on testhead 11 (FIG. 1) includes two thumb switches 28A and 28B which allow the operator to activate and control the system without leaving the test area. An LED display 29 on control panel 27 provides the operator with information pertinent to the test sequence. A cable outlet or connector 30 is connected via a single interconnecting cable (not shown in FIG. 2) to a corresponding outlet on control system interface 25 (FIG. 1). Cables from microphones 17A and 17B may be routed down the length of waveguide 12 and electrically coupled to pins of connector 30 so that the signals are carried by the interconnecting cable to signal conditioner 18 of FIG. 1. Quick release connectors (not shown) may be provided at some point along the length of the cables to facilitate connection if a microphone must be replaced. Further, a partially cylindrical sheath (not shown) may be affixed to waveguide 12 so as to shield microphones 17A and 17B and the cables extending therefrom, from mechanical abuse during the testing procedure.

Referring to FIG. 1, memory 20B of computer 20 stores captured test data for post-processing and allows for the transfer of calculated data to a removable floppy disc in disc drive 22 for further analysis. The spectrum analyzer 16 measures the sound pressure spectrum from each transducer and calculates a frequency response function, which is required to calculate the acoustic resistance. The system is completely automated, requiring only minimal training to operate.

Referring to FIG. 2A, control panel 27 acts as the lower wall of a housing 31 which surrounds the driver 13. A series of bolts 32 secures panel 27 to housing 31. A metal plate 34 has a planar portion 35 with a circular cut out for receiving the lower conical portion 36 of driver 13. Plate 34 has two extensions 37A and 37B angled downwardly with respect to planar portion 35 and having cut outs therein so that extensions 37A and 37B may serve as handles for head 11, allowing an operator to manipulate head 11 so that gasket 26 forms a seal against a liner to be measured. Four bolts 39 serve to secure planar portion 35 of plate 34 to driver 13 and extend through holes therein and holes in an integral upper cover 40 of housing 31 which is held against a surface of driver 13 by the action of bolts 39 and nuts 41.

Referring to FIG. 1, preparation of the system for measurements of a fully assembled liner requires a series of calibration steps. Initially both pressure transducers (microphones 17A and 17B) are calibrated to a known sound pressure level. This is accomplished by placing each transducer and a fully calibrated reference microphone in the same acoustic pressure field such as the field generated by a pistophone, which has a calibration traceable to the National Bureau of Standards. The sensitivity of the system to the output of the pressure transducer is adjusted within spectrum analyzer 16 to yield the same pressure reading as the reference microphone.

Figure 3:
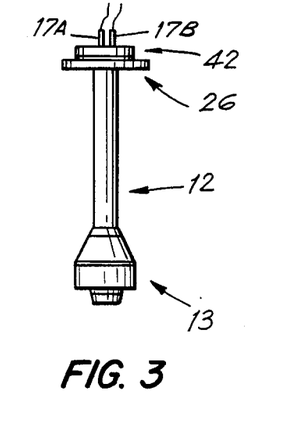
FIG. 3 is a side elevational view of an arrangement used for laboratory calibration of the system of FIG. 1.

To accommodate a daily field calibration, the magnitude and phase difference between the two transducers must be measured. An arrangement for accomplishing this is shown in FIG. 3. The two transducers or microphones 17A and 17B are mounted side by side in an acoustically reflective metal plate 42. The openings in the wall of waveguide 12 which normally accommodate microphones 17A and 17B are temporarily filled with steel rods of the same diameter as that of microphones 17A and 17B. Plate 42 is sealed with the transducers in the center of waveguide 12, against gasket 26 at the top of waveguide 12. Driver 13 is used to generate an acoustic oscillating pressure at the test frequency which corresponds to the resonant frequency of the liner. At a low acoustic pressure level, the frequency response function of the microphones is measured with the spectrum analyzer 16. The real and imaginary parts of the complex number representing the response are stored in the memory 20B of computer 20. This measurement is repeated at successively higher acoustic pressure levels to establish magnitude and phase differences between the microphones, with the levels corresponding to levels that will be used to test the assembled liner 10. This establishes absolute data concerning the magnitude and phase characteristic that is unique to the set of microphones being used.

To calibrate the system in the field, without removing the transducers from waveguide 12 (as is required by the arrangement of FIG. 3) a test sample with unchanging acoustic properties is required. Sample 47 of FIG. 4 meets these requirements. Sample 47 consists of a perforated plate facing sheet 49, guide pins 48 extending perpendicularly therefrom to ensure repeatable rotational and longitudinal alignment with waveguide 12 by being received in corresponding slots therein (not shown) for pins 48, a cylindrical cavity 47 with the same inside diameter as that of waveguide 12 and a solid back skin 46 which provides a highly reflective surface.

With the magnitude and phase difference between microphones 17A and 17B having been established in the laboratory by use of the arrangement of FIG. 3, the actual acoustic properties of sample 47 are measured. After placing sample 47 on open end 12A of waveguide 12, acoustic pressure source 13 is activated. Again, a low level sinusoidal plane wave pressure field is propagated through waveguide 12 against sample 47. The frequency response function is then measured with microphones 17A and 17B and spectrum analyzer 16. The complex frequency response measurement data is then divided by the transducer magnitude and phase correction factor measured at a similar level. The result is the corrected frequency response function for the sample at that level and frequency. These numbers are stored in memory 20B of computer 20 for later use in a field calibration procedure. This measurement is repeated at each level that is to be used in the measurement procedure.

Figure 4:
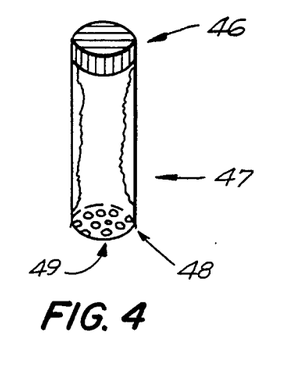
FIG. 4 is a partially cut away perspective view of a field calibration standard used with the system of FIG. 1.

To calibrate the system in the field, the calibrated sample shown in FIG. 4 is placed on open end 12A of waveguide 12. Driver 13 is driven with a sinusoidal plane wave at the same frequency and levels as used to measure the actual frequency response data. At each level the apparent frequency response function is measured. This data is divided by the actual frequency response data. The result is the complex number which describes the magnitude and phase difference between the transducers. As noted, the purpose of the calibration sample is to establish magnitude and phase differences between the transducers without removing them from their locations within waveguide 12. This field calibration step corrects for changes in ambient conditions such as temperature, humidity, etc., in the field which may have adverse effects on system accuracy. In most environments it need be performed no more than once a day.

Figure 5A:
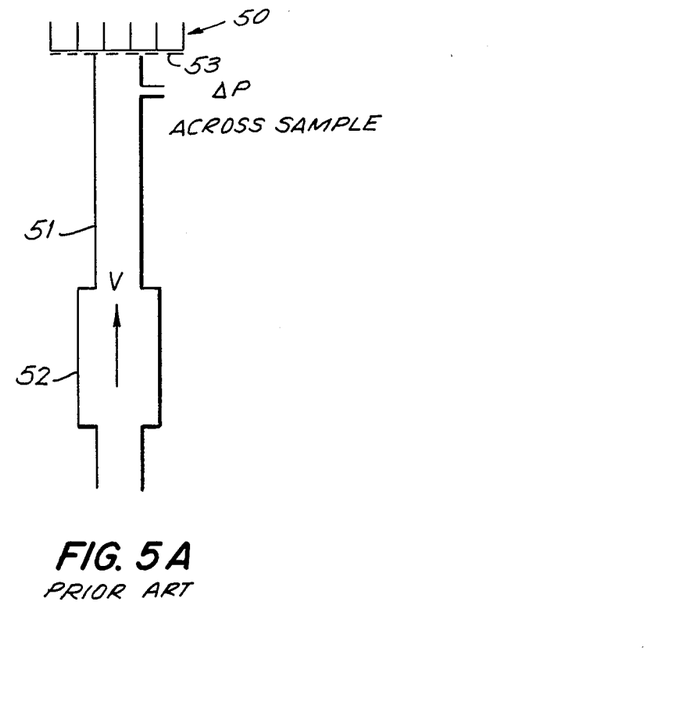
FIG. 5A is a schematic diagram of a conventional DC flow acoustic resistance measurement system.
Figure 5B:
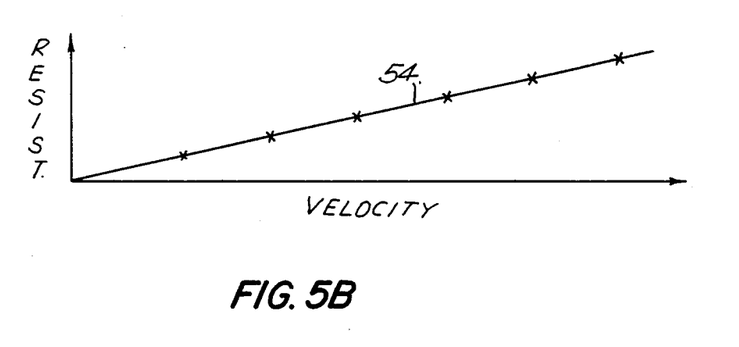
FIG. 5B is a conventional plot of DC flow resistance as a function of flow velocity produced with data obtained from the system of FIG. 5A.

A final correction procedure is performed to account for measurement distortion which may arise from effects such as cell misalignment, transverse wave propagation within the cells and energy transmission through the backing plate. This is done by measuring the DC flow resistance and non-linearity of a liner sample identical in construction to the fully assembled liner which is to be measured in the field. The apparatus shown in FIG. 5A is used to make this measurement of DC flow resistance. A liner sample 50, without a back skin, is fixed against the opening of an air flow tube 51. With the air flowing at a steady rate, the velocity is measured using a laminar flow element 52. The pressure drop across the sample is measured by measuring the pressure at the sample face 53 and correcting the measurement for atmospheric conditions. The resistance of the specimen at this test location is calculated from the ratio of the pressure drop across the sample to the velocity impinging upon the sample face. By increasing the flow rate and repeating this measurement at a number of velocities, the non-linear properties of the liner can be measured. A least squares curve fit algorithm is used to fit a line through the test points and an equation for straight line 54, as shown in FIG. 5B, is generated. The non-linear behavior of the resistance of the sample as a function of velocity is defined from the equation derived from line 54.

Figure 6:
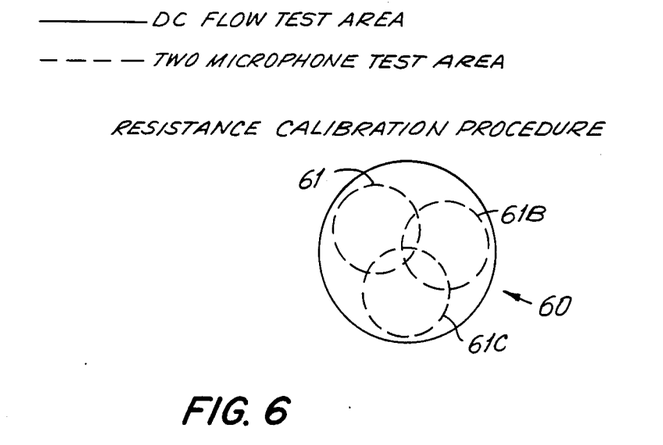
FIG. 6 is a diagram illustrating the manner in which data is obtained to correlate the results produced using the systems of FIG. 1 and FIG. 5A.
Figure 7:
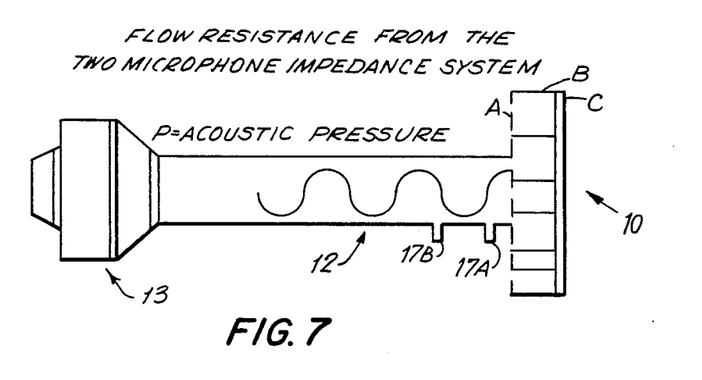
FIG. 7 is a schematic diagram further illustrating the manner of acquiring data with the system of FIG. 1.

The procedure used to correlate the acoustic test procedure with measurements obtained using steady state flow conditions, is best understood by referring to FIG. 6. The DC flow resistance measurement is performed over a surface area of the specimen enclosed by circle 60 having a diameter of 2.074 inches. Once the DC flow resistance test is completed, a back sheet is bonded to the specimen. Honeycomb core depth is maintained equivalent to the depth used on the fully assembled production liner. Within the test area used for the DC flow resistance measurements, three separate tests are performed to determine resistance and non-linearity of resistance using the apparatus of FIG. 1. Circular areas 61A, 61B and 62C of 1.2 inches in diameter are used for these tests. The acoustic measurement tests are performed as described in FIG. 7. Testing is started by positioning waveguide 12 against the face sheet A of sample 10 as shown in FIG. 7. An acoustic sinusoidal pressure is generated by driver 13. The frequency of the signal is adjusted to coincide with the resonant frequency of the liner test sample 10. The frequency response function of the two transducers or microphones 17A and 17B is measured for pressure level magnitudes used during initial calibration of the system. The response function is adjusted to account for magnitude and phase differences between the transducers by using results obtained from the previous calibration procedures. The corrected frequency response function is used to determine the acoustic resistance at each acoustic pressure level. At each acoustic pressure level the rms (root mean square) pressure magnitude at the transducer nearest the sample face is measured and recorded.

It has been confirmed that with the testing being done at the resonant frequency of the liner, the pressure on the back of the sample face is on the order of 30 dB below that at the face. Therefore, the rms pressure measured at the sample face is equated to the static pressure drop measured with the DC flow system. Thus, the rms velocity of the oscillating pressure, which is equated to the steady state flow velocity of the DC flow system, can be calculated from the ratio of the rms pressure at the first transducer to the measured acoustic resistance. Using the data from each acoustic pressure test level, a least squares curve fit algorithm can be used to fit a straight line through the data points. This measurement sequence is performed with waveguide 12 positioned at each of the locations indicated in FIG. 6 by circles 61A, 61B and 61C. The lines describing the non-linear resistance for each acoustic measurement location are averaged to produce a line equation equivalent to that measured with the DC flow system. More specifically, the slopes of the straight line equations and the Y intercepts of the straight line equations are averaged to produce respectively, the slope and Y intercept of the average equation. A typical plot is represented by line 62 in FIG. 8. Line 63 represents corresponding DC flow data.

Figure 8:
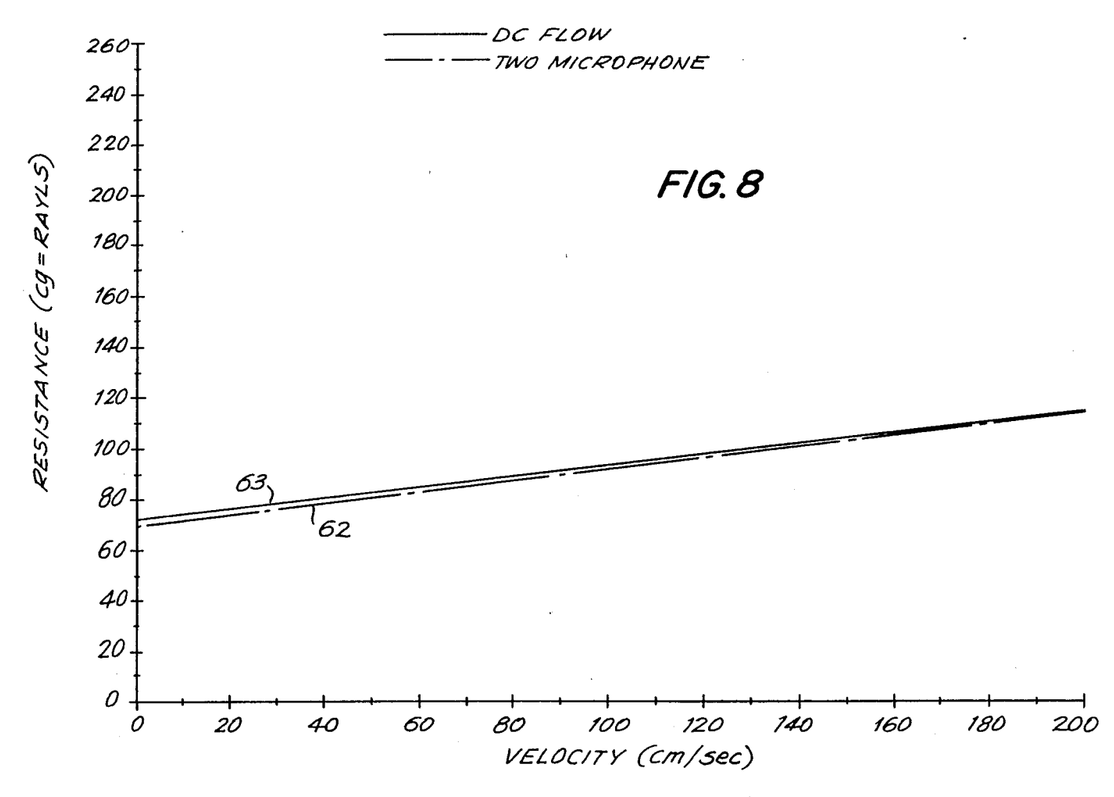
FIG. 8 illustrates the agreement of data obtained by DC flow resistance measurements and by using the system of FIG. 1.

The error between line 62 and line 63, is generally on the order of one to three percent. This error is caused by the sample characteristics previously discussed. The error is compensated for by numerically correcting the averaged line equation for the acoustic measurement to fit the DC flow line equation. This correction is then used for all measurements made on liners of identical construction.

The general equations used to convert the pressure measurements obtained by microphones 17A and 17B to data indicative of the acoustic properties of a material are well known. These equations have been developed by J. Y. Chung and D. A. Blaser, in "Transfer Function Method of Measuring In-Duct Acoustic Properties 1. Theory, 2. Experiment," Journal of the Acoustic Society of America, Vol. 68, No. 3, pp 907–921, September, 1980. However, the theoretical basis for two microphone techniques was first developed by A. F. Seybert and D. F. Ross, in "Experimental Determination of Acoustic Properties Using a Two-Microphone Random-Excitation Technique, Journal of the Acoustical Society of America, Vol. 61, No. 5, pp. 1362–1370, May, 1977 and by A. F. Seybert and B. Soenarko, in "Error Analysis of Spectral Estimates With Application to the Measurement of Acoustic Parameters Using Random Sound Fields in Ducts," Journal of the Acoustical Society of America, Vol. 69, No. 4, pp. 1190–1199, April, 1981. These equations permit a measurement of the magnitude of the acoustic pressure incident upon a sample, and the magnitude of the reflected pressure wave, thereby defining the standing wave ratio, and the acoustic impedance of the sample, which also defines the acoustic resistance. Computer 20 may be programmed to utilize these equations, by one skilled in the art.

Figure 9:
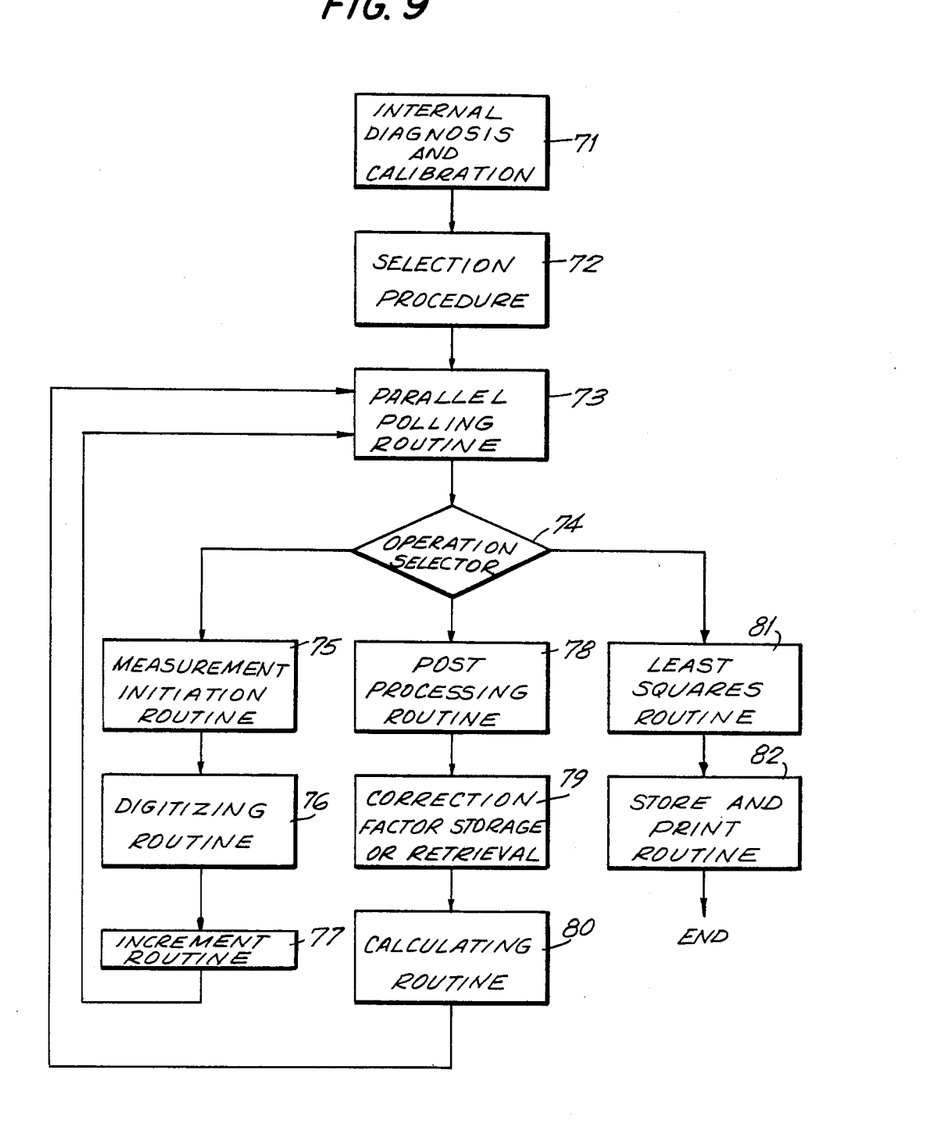
FIG. 9 is a flow chart of the operation of the system of FIG. 1.

A flow chart of the operation of the system of FIG. 1 is shown in FIG. 9. Upon the application of power to the system, the computer 20 (hereinafter referred to as controller 20) goes through a series of internal diagnostic and calibration procedures 71. After completion of these procedures, information is sent by controller 20 over bus 21 to interface 25 to illuminate an LED in display 29 of control panel 27, thus indicating that the system is ready for operation.

After positioning the open end 12A of waveguide 12 against a calibration sample or an actual liner to be tested, the selection procedure 72 is initiated by the operator when one of thumb switches 28A or 28B is activated. Switch 28A is used to indicate that a calibration is to be performed, while switch 28B indicates that a liner is to be tested. Activating either switch causes the system interface unit 25 to generate a request for service on bus 21. Controller 20 initiates a parallel polling routine 73, which is used to define what address on bus 21 generated the request. Each switch 28A and 28B has a different identification code, which is decoded to cause appropriate operation to be initiated by operation selector 74.

Whether a calibration procedure is performed or a measurement is being taken, oscillator 15 in spectrum analyzer 16 is turned on by measurement initiation routine 75, which partially transfers control of the system to spectrum analyzer 16. Power amplifier 14 provides power to driver 13 at the lowest (first) acoustic power measurement level. Spectrum analyzer 16 sets the appropriate input voltage range for each channel so as to acquire the time waveform data.

The time waveform data which is acquired is digitized by spectrum analyzer 16 during digitizing routine 76. The digitized data is fed directly to disc drive 22 via bus 21. A service request is then generated by analyzer 16 to indicate completion of data transfer. A power level incrementing routine 77, which is essentially a counter, is then incremented so that when control is again transferred to analyzer 16, power amplifier 14 will provide power to driver 13 at the next measurement level. However, control is transferred back to controller 20 and parallel polling routine 73 is again executed. Operation selector 74 then causes measurement routine 75 to again be executed at the higher power level specified by power level incrementing routine 77.

Execution of the data acquisition loop consisting of polling routine 73, operation selector 74, measurement initiation routine 75, digitizing routine 76 and power level incrementing routine 77 is repeated until incrementing routine 77, after being set to a count representing the highest acoustic power level, resets itself automatically to a count representing the lowest acoustic power level. The input sensitivity of spectrum analyzer 16 is appropriately adjusted for each measurement. A signal is then supplied to operation selector 74 indicating that the measurement has been completed.

Operation selector 74, upon completion of data acquisition, then selects post processing routine 78, to perform a series of post processing steps on the data accumulated at the first acoustic pressure level. Control is shifted to analyzer 16 which recalls the digitized time data from the disc in disc drive 22 by way of bus 21. Analyzer 16 uses a Fast Fourier Transform (FFT) to convert the data from the time domain into the frequency domain. The spectral data is averaged to represent the mean spectral levels. A service request is then generated on bus 21 by analyzer 16 indicating completion of processing.

Controller 20 again acquires control and the processed data produced by post processing routine 78 is used by calculating routine 80 to calculate resistance and velocity as set forth above. Before calculating routine 80 is executed, a correction factor storage or retrieval routine 79, that either stores or retrieves the calibration data obtained during the calibration procedure set forth above, is executed. If selection procedure 72 has noted that calibration is taking place, then data is stored. If an actual sample test is being performed, then the stored values are recalled for use by calculating routine 80.

The processing loop consisting of polling routine 73, operation selector 74, post processing routine 78, correction factor storage or retrieval routine 79 and calculating routine 80 is repeated a number of times equal to the number of acoustic pressure levels at which measurements have been made. The data produced by each calculation is stored in memory 20B.

Operation selector 74 then branches to least squares curve fit routine 81 which provides the equation of a straight line that represents the nonlinear properties of the resistance.

After the least squares curve has been generated, the data representing the curve is stored on a disc in disc drive 22 and printed by the printer 23, under the control of store and print routine 82. If the printer does not have graphics capability, printer 23 and plotter 24 are used. Thus, not only is a hard copy printout generated, but the data is also available on disc so that it can be evaluated at a later time.

If one of microphones 17A or 17B must be replaced, the entire calibration procedure set forth above is repeated to assure that the acoustic resistance is accurately determined by the system.

Although shown and described in what are believed to be the most practical and preferred embodiments, it is apparent that departures from the specific method and designs described and shown will suggest themselves to those skilled in the art and may be made without departing from the spirit and scope of the invention. We, therefore, do not wish to restrict ourselves to the particular construction described and illustrated, but desire to avail ourselves of all modifications that may fall within the scope of the appended claims.

We claim:

1. A method for determining the steady state flow resistance of a sound absorbing material to steady state air flow through the sound absorbing material at an air flow velocity, comprising the steps of:
   placing an open end of an acoustic waveguide in contact with the sound absorbing material;
   exciting, without said steady state air flow through said sound absorbing material, air in the waveguide with an acoustic signal;
   measuring the acoustic pressure level at a first point and a second point along said waveguide proximate the open end in contact with said material;
   calculating an acoustic impedance of the sound absorbing material based on values of the pressures determined at said first point and said second point to provide an acoustic resistance of said sound absorbing material; and
   dividing the pressure at the first point by the acoustic resistance to determine the velocity.

2. The method of claim 1, wherein said step of exciting the waveguide is performed with an acoustic signal having a frequency corresponding to a resonant frequency of the sound absorbing material.

3. The method of claim 1, wherein said acoustic signal is varied in amplitude, to determine said flow resistance as a function of velocity.

4. The method of claim 3, wherein said flow resistance is determined at a first velocity and a second velocity, further comprising the step of dividing the flow resistance at said first velocity by the flow resistance at said second velocity to establish a non-linearly factor.

5. The method of claim 1, wherein said sound absorbing material includes a honeycomb layer.

6. The method of claim 5, wherein said sound absorbing material further comprises a face sheet assembled to one side of said honeycomb layer and a backing sheet assembled to another side of said honeycomb layer, said end of said waveguide being placed in contact with said face sheet.

7. The method of claim 6, wherein said step of exciting the waveguide is performed with an acoustic signal having a frequency corresponding to a resonant frequency of the sounding absorbing material in a direction of the thickness thereof.

8. The method of claim 6, further comprising the step of calculating the acaustic reactance of the face sheet based on values of pressures determined at said first point and said second point.

9. The method of claim 1, wherein the acoustic signal is of a wavelength sufficiently high in relation to the dimensions of said waveguide so that plane acoustic waves are propagated along said waveguide.

10. The method of claim 1, further comprising the step of:
    performing an absolute calibration of a first transducer and a second transducer;
    said first transducer being used to determine the acoustic pressure level at the first point and said second transducer being used to determine the acoustic pressure level at the second point.

11. The method of claim 10, further comprising the steps of:
    placing said first transducer and said second transducer at points of equal phase in a coherent acoustic field at a frequency and at acoustic pressure levels used for measurement;
    measuring a first value of the frequency response function; and
    recording the first value measured.

12. The method of claim 11, further comprising the steps of:
    placing a calibration sample of known acoustic properties over the open end of said waveguide;
    measuring a second frequency response function;
    dividing the second frequency response function measured by the first values to define corrected frequency response function values; and
    storing the corrected frequency response function values.

13. The method of claim 12, further comprising the steps of:
    placing said calibration sample over the end of said waveguide;
    measuring an apparent frequency response function to define values therefor;
    dividing the values of the apparent frequency response function by the corrected frequency response function values to define absolute magnitude and phase differences in response of the transducers.

14. The method of claim 15, further comprising the steps of:
    measuring the steady state flow resistance of a liner without a backing sheet at selected flow velocities, the liner being identical in construction to one to be measured;
    correlating the determined flow resistance values with the corresponding measured DC flow resistance values.

15. The method of claim 1, wherein said sound absorbing material is a fully assembled and bonded acoustic liner.

16. The method of claim 1, wherein said first point is located a distance along said waveguide from said sound absorbing material, said distance being a small fraction of a wavelength of said acoustic signal, and said second point is located a distance other than any integer multiple of one quarter wavelength of said acoustic signal from said first point in a direction along said waveguide away from said sound absorbing material.

17. An apparatus for determining the flow resistance of a sound absorbing material to steady state air flow through the sound absorbing material at an air flow velocity, comprising:
   an acoustic waveguide having an open end for contacting the sound absorbing material;
   an acoustic signal generating means associated with said waveguide for producing an acoustic signal, without said steady state air flow through said sound absorbing material, in said waveguide;
   a first acoustic pressure sensing means disposed at a first point along said waveguide, said first acoustic pressure sensing means being for measuring a first signal representative of acoustic pressure in said waveguide at said first point;
   a second acoustic pressure sensing means disposed at a second point along said waveguide, said second acoustic pressure sensing means being for measuring a second signal representative of acoustic pressure in said waveguide at said second point;
   analyzing means responsive to said signals from said first and second acoustic pressure sensing means, said analyzing means including:
   calculating means for calculating acoustic impedance of said sound absorbing material in accordance with complex pressure representation of said signals to provide an acoustic resistance of said sound absorbing material and for dividing a value of magnitude of pressure at said first point by the acoustic resistance to determine the velocity.

18. The apparatus of claim 17, further comprising frequency adjusting means for adjusting the frequency of the acoustic signal so that it is equal to a resonant frequency of the sound absorbing material.

19. The apparatus of claim 17, further comprising amplitude adjusting means for adjusting the amplitude of the acoustic signal in said waveguide to vary said velocity.

20. The apparatus of claim 17, in combination with said sound absorbing material, wherein said sound absorbing material comprises a honeycomb layer, a face sheet assembled to one side of said honeycomb layer and a backing sheet assembled to another side of said honeycomb layer opposite said first side, said end of said waveguide being placed in contact with said face sheet.

21. The combination of claim 20, wherein said face sheet and said backing sheet are bonded to opposite sides of said honeycomb layer.

22. The apparatus of claim 21, further comprising additional calculating means for calculating the mass acoustic reactance of said face sheet.

23. The apparatus of claim 17, wherein the acoustic signal frequency and dimensions of said waveguide are related so that plane acoustic waves are propagated along said waveguide.

24. The apparatus of claim 17, in combination with said sound absorbing material, said sound absorbing material being a fully assembled and bonded acoustic liner.

25. The apparatus of claim 17, wherein said first point is located a distance along said waveguide from said sound absorbing material, said distance being a small fraction of a wavelength of said acoustic signal, and said second point is located a distance of other than any integer multiple of one quarter wavelength of said acoustic signal from said first point, in a direction along a said waveguide away from said sound absorbing material.

* * * * *

UNITED STATES PATENT AND TRADEMARK OFFICE
CERTIFICATE OF CORRECTION

PATENT NO. : 4,768,379

DATED : September 6, 1988

INVENTOR(S) : NOE ARCAS ET AL

It is certified that error appears in the above-identified patent and that said Letters Patent is hereby corrected as shown below:

Col. 3, lines 40 and 41, "adJusted" should be -- adjusted --

Col. 5, line 32, "mV/PA" should be -- $\mu$V/PA --

Col. 12, line 9, which is claim 8, "acaustic" should be -- acoustic -- line 54, which is claim 14, "15" shculd be -- 13 -- line 61, which is claim 14, "DC" should be -- steady state --

Signed and Sealed this

Twenty-fourth Day of July, 1990

Attest:

HARRY F. MANBECK, JR.

*Attesting Officer*   *Commissioner of Patents and Trademarks*